US00PP22593P3

(12) United States Plant Patent
Garnighian

(10) Patent No.: US PP22,593 P3
(45) Date of Patent: Mar. 20, 2012

(54) ***STEVIA* PLANT NAMED 'T60'**

(50) Latin Name: ***Stevia rebaudiana* L.**
Varietal Denomination: T60

(75) Inventor: Grania Viorela Garnighian, Prior Lake, MN (US)

(73) Assignee: SGF Holdings LLC, Bellingham, WA (US)

( * ) Notice: Subject to any disclaimer, the term of this patent is extended or adjusted under 35 U.S.C. 154(b) by 0 days.

(21) Appl. No.: 12/799,668

(22) Filed: Apr. 28, 2010

(65) Prior Publication Data

US 2011/0271413 P1 Nov. 3, 2011

(51) Int. Cl.
*A01H 5/00* (2006.01)

(52) U.S. Cl. ..... Plt./258

(58) Field of Classification Search ..... Plt./258, Plt./263.1

See application file for complete search history.

*Primary Examiner* — Susan McCormick Ewoldt

(74) *Attorney, Agent, or Firm* — Morrison & Foerster LLP

(57) ABSTRACT

A new and distinct *Stevia rebaudiana* plant named 'T60' is described. The new variety is distinguished from other *Stevia* varieties by a high leaf concentration of rebaudioside A; its tall, bushy nature; its ovate leaves; and its long stem stature.

1 Drawing Sheet

Botanical/commercial classification: *Stevia rebaudiana* L.
Variety denomination: 'T60'.

BACKGROUND OF THE INVENTION

*Stevia rebaudiana* is a shrubby perennial, growing up to 65-100 cm tall. It is a member of the Compositae family and originates from Paraguay. This species is grown commercially in Brazil, China, Paraguay, the United States, and other countries. The plants are grown so that sweet glycosides present in the leaves can be extracted for use as sweeteners. The sweetest of these glycosides is rebaudioside A (Reb A).

The development of new varieties of *Stevia rebaudiana* with high levels of Reb A is desirable. The new *Stevia* variety 'T60' described herein is such a variety.

The new 'T60' variety was asexually reproduced from callus through an in vitro tissue culture technique performed in Woodland, Calif.

BRIEF SUMMARY OF THE INVENTION

The major characteristics exhibited by the new *Stevia* variety 'T60' that distinguish it from other varieties include a high concentration of total glycoside and high concentration of Reb A in the leaves from total glycoside. Other major characteristics that also distinguish the new *Stevia* variety 'T60' from other varieties include a tall, bushy stature that is resistant to high winds; spatulate-oblanceolate to ovate leaves; high yield foliage production. For example, 'T60' produced over 3000 lbs/acre in one harvest. Still other major characteristics that distinguish the new *Stevia* variety 'T60' from other varieties include being virus free, resistant to *Fusarium* ssp. and *Sclerotinia* ssp., drought resistant, and resistant to compact argilous soils. Another major characteristic exhibited by the new *Stevia* variety 'T60' that distinguishes it from other varieties is an average biological cycle of 90-115 days between 20-27 N,S Latt, giving the option of secondary harvest per annual cycle.

DETAILED DESCRIPTION OF THE INVENTION

Figure 1:
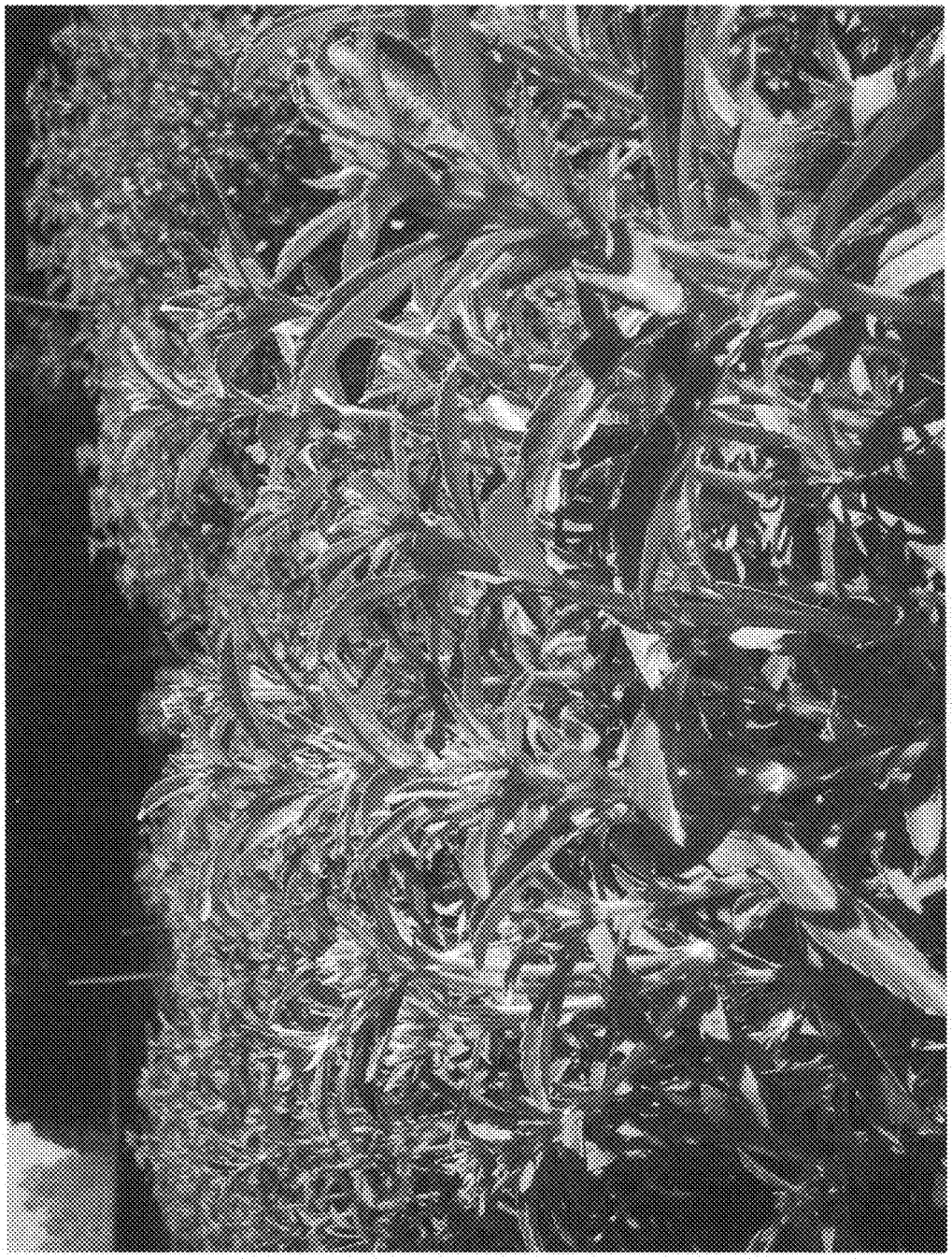
FIG. 1 depicts a color photograph of a fully mature 'T60' *stevia* plant near the end of the growing season.

Four wild varieties of *Stevia* were imported from the Paraguayan government. These varieties were derived from a wild germ plasm in Paraguay, locally identified as 'Criola' material, and released by the Paraguayan government upon request for research and breeding. The four imported 'Criola' lines were named 'IAN-135', 'IAN-142', 'IAN-228', and 'IAN-259'.

Table 1 depicts the glycoside and Reb A percentages for the 'Criola' lines described above.

TABLE 1

| Variety | Cycle | Flowering Days | Plant Height (cm) | Length of Leaves (cm) |
|---|---|---|---|---|
| IAN-228 | Early | 110 | 65 | 4 |
| IAN-135 | Medium | 180 | 82 | 4 |
| IAN-259 | Medium | 180 | 55 | 5 |
| IAN-142 | Late | 200 | 110 | 6 |

| Variety | Width of Leaves (cm) | Total Glycoside | Total Reb A | Reb A to Glycoside |
|---|---|---|---|---|
| IAN-228 | 2 | 18.47 | 13.25 | 71.7% |
| IAN-135 | 2 | 16.56 | 8.06 | 48.7% |
| IAN-259 | 2 | 16.55 | 11.24 | 67.9% |
| IAN-142 | 3 | 19.06 | 13.15 | 69% |

As a first step in the production of new *Stevia* varieties, the four 'Criola' lines were planted in vitro in tissue culture medium. The tissue culture material was multiplied by successively transferring plantlets in hormone-supplemented culture. Plantlets of each variety were planted into 2 inch plugs and then into 4 inch pots between December of year 1 and January of year 2. The plantlets were planted in a field in Woodland, Calif. between March and April of year 2. The plantlets were then allowed to flower, which occurred between July and August of year 2.

In August of year 2, anthers from the flowered plantlet were collected before anthesis. Approximately 200 anthers were collected from plantlets of each of the four 'Criola' lines. The anthers were then plated in vitro to derive haploid lines. The in vitro tissue culture medium induced callus formation from the plated anthers. Callus formation was observed in October of year 2. Haploid lines were created from the formed callus. The process of creating elite *Stevia* lines required that the chromosome count of each haploid line be doubled, since haploid lines cannot survive as plants. The full complement of chromosomes was regenerated by using successive colchicine treatments of 20 ppm, 40 ppm, and 60 ppm on both the callus and the shoots regenerated from the callus.

Every green callus that formed a diploid plantlet was transferred into a hormone-free medium for multiplication. Multiplication of the diploid plantlets resulted in the creation of a unique line of plants with unique characteristics distinguishable form the original four 'Criola' lines. These new *Stevia* lines were named T-lines. The T-lines were grown out in 2 inch plugs, then transferred to 4 inch pots, and then planted in the field in Woodland, Calif. The selected T-lines were shown to be superior to the parental stock. The selected T-lines either had higher total levels of glycoside, or higher levels of Reb A. Based on these characteristics, all callus material that gave rise to the new T-lines was collected. Genetically unique lines were developed from this callus material.

To test for percentage of Reb A production, the new T-lines were planted from tissue culture into 2 inch plugs and then transplanted into 4 inch pots. By the age of six weeks, this second generation of T-line plants had grown to about 10 inches in height in the pots. At six weeks the T-line plants were sampled to obtain HPLC data on the percentage of Reb A production. This was done even though the percentage of glycosides found in the leaf material of the new T-lines plants would not be as high as expected levels in mature plants. The levels of Reb A in these new T-line *Stevia* plants were as high as 89.2% of total glycoside levels. After the HPLC data was obtained, the T-line *Stevia* plants were planted in the field in Woodland, Calif., and grown to maturity. At maturity, the production rates of glycosides were evaluated.

All new T-lines were grown out in greenhouses in Woodland, Calif. for planting in the field, to allow for further testing and breeding for seed.

Of the new *Stevia* T-lines, three varieties were selected that produced high levels of Reb A. The production of high levels of Reb A in these *Stevia* T-lines will allow large amounts of Reb A to be harvested. The present *Stevia* variety 'T60' is one of the three selected T-lines developed by the methods described herein. The *Stevia* variety 'T60' was derived from the T-line 'T6'. The 'T6' line was derived from 'Criola' line 'IAN-135'.

Table 2 depicts HPLC data on the percentage of glycoside and Reb A for samples of the *Stevia* variety 'T60'.

TABLE 2

| Samples of mature 'T 60' *Stevia* plants | Total Glycoside | Total Reb A | Reb A to Glycoside |
|---|---|---|---|
| 09-0144 | 15.18 | 12.58 | 82.8% |
| 09-0154 | 16.96 | 14.39 | 84.8% |
| 09-0165 | 14.58 | 12.00 | 82.3% |
| 09-0166 | 15.05 | 12.46 | 82.8% |

The HPLC data shows that the average percentage of Reb A to Glycoside in *Stevia* variety 'T60' was 83.2%. This is an increase of at least 11.5% over the 'Criola' lines. The 'T60' variety also showed an increase of 34.5% over 'IAN-135', from which 'T60' is derived.

DETAILED BOTANICAL DESCRIPTION

The *Stevia* variety 'T60' is a perennial herb with filiform deep roots. The 'T60' variety has a long stem that is on average 65-100 cm tall, erect, hairy, and slender. The stem easily produces secondary shoots (suckers) from its base, dies off and is renewed annually. The stem produces an average of 5 to 10 suckers. The stem also produces numerous lateral branches, thus, forming a more-or-less roundish and dense crown. The 'T60' variety also has an average biological cycle of 90-115 days. The variety goes dormant and is renewed annually.

The stem of the 'T60' variety produces an average of 3 to 7 lateral branches. The average length of each lateral branches ranges from 30 to 40 cm. The average diameter of the lateral branches ranges from 5 to 7 mm. The lateral branches are light green in color (RHS 142A). The lateral branches form a roundish and dense crown.

The crushed leaves exude a strong odor, and all the green parts of the plant taste sweet. The leaves are simple, opposite and sub sessile. The internodes have an average length of 2 to 4 cm. The blades are subcoriaceous, very variable in shape and size, and ovate. The blades have an average length of 2 to 3 cm and an average width of 0.6 to 1 cm. The blades are apex obtuse, base cuneate, margins entire serate on the upper half, three primary veins arise from the leaf base raised and prominent on the blade's lower side, immersed on the upper side, and secondary venation reticulate.

The leaf blades of actively growing plants of the 'T60' variety are light green in color (RHS 142A). In the dry state, the leaf blades are olive-green to brownish green in color (RHS 147A-147B), and usually darker on the upper side. Both surfaces are subscabrous with black glandular dots on the lower side, the leaves sub sessile or the petiole to 3-4 mm long. The capitula are arranged into loose, paniculate corymbose inflorescences at the terminal ends of the branches, and have a peduncle that is on average 1-4 cm long, and very slender. Pedicels of each capitulum are slender and on average are 1-4 mm long, bracts are linear-lanceolate, and on average are 1-2 mm long. Each capitulum is enveloped by an involucre, and the lower half has a light green color (RHS 142A), and the upper half has a yellowish (RHS 142C) color. The stems at maturity are brown-reddish in color (RHS 35A-35B).

The *Stevia* variety 'T60' has 5 phyllaries that are finely hairy, green (RHS 129B) when fresh, linear to subulate, 4-5 mm long, and acute to rounded at apex. Each capitulum is made up to 5 disk florets greenish white (RHS 155C). The seeds are achenes bearing numerous, equally long pappus awns.

The *Stevia* variety 'T60' expresses high concentrations of total glycosides, with a total of rebaudioside A concentration of greater than 80%. The *Stevia* variety 'T60' has an average biological cycle of 90-115 days.

We claim:

1. A novel and distinct variety of *Stevia* plant named 'T60' having the characteristics described and illustrated herein.

* * * * *